United States Patent
Bonnet et al.

(10) Patent No.: US 9,149,622 B2
(45) Date of Patent: Oct. 6, 2015

(54) SECURE FLUIDS TRANSFER SYSTEM FOR MEDICAL USE

(75) Inventors: Frederic Bonnet, Bayonne (FR); Francois Capitaine, Anglet (FR)

(73) Assignee: TECHNOFLEX, Bidart (FR)

( * ) Notice: Subject to any disclaimer, the term of this patent is extended or adjusted under 35 U.S.C. 154(b) by 600 days.

(21) Appl. No.: 13/424,717

(22) Filed: Mar. 20, 2012

(65) Prior Publication Data
US 2013/0245611 A1    Sep. 19, 2013

(51) Int. Cl.
*A61M 39/10*    (2006.01)

(52) U.S. Cl.
CPC ....... *A61M 39/10* (2013.01); *A61M 2039/1027* (2013.01); *A61M 2039/1033* (2013.01); *A61M 2039/1038* (2013.01)

(58) Field of Classification Search
CPC . A61M 39/10; A61M 39/1011; A61M 39/12; A61M 2039/1027; A61M 2039/1033; A61M 2039/1038
USPC .................. 604/523, 533, 535, 537, 539, 905
See application file for complete search history.

(56) References Cited

U.S. PATENT DOCUMENTS

| | | | | |
|---|---|---|---|---|
| 2005/0020980 | A1* | 1/2005 | Inoue et al. | 604/152 |
| 2007/0129705 | A1* | 6/2007 | Trombley et al. | 604/523 |
| 2008/0086087 | A1* | 4/2008 | Spohn et al. | 604/151 |
| 2008/0287919 | A1* | 11/2008 | Kimball | 604/533 |
| 2011/0178496 | A1* | 7/2011 | Grant | 604/500 |

* cited by examiner

*Primary Examiner* — Theodore Stigell
*Assistant Examiner* — Amber Stiles
(74) *Attorney, Agent, or Firm* — Young & Thompson

(57) ABSTRACT

A fluid transfer system includes a Luer female connector having a main body containing an internal channel for passage of fluids and a collar surrounding at least a part of the end of the main body, and a Luer male connector having a main body with a longitudinal internal opening. The main body of the female connector contains a first threading on at least a part of the external surface of that portion that is surrounded by the collar, located at least in part facing an internal surface of the collar; one of the ends of the main body of the Luer male connector contains a second threading on at least a part of its internal surface delineating the longitudinal internal opening, which engages into and fits in the first threading to ensure joining between the Luer male and female connectors.

11 Claims, 7 Drawing Sheets

SECURE FLUIDS TRANSFER SYSTEM FOR MEDICAL USE

BACKGROUND OF THE INVENTION

1. Domain of the Invention

This invention is in the field of Luer connections, specifically a secure mechanism for the transfer of medical use solutions.

2. Technological Background

It is a well-known practice to use Luer connections to connect for example medical devices to each other for introducing medical solutions from a primary recipient to ducts within human bodies.

FIGS. 1 and 2 show state of the art Luer male and female connectors. A Luer male connector 1 comprises a collar 2 encircling at least a part of the conical male part 3 whose external surface joins to the female conical connecting surface of the Luer female connector 4 when these Luer male 1 and female 4 connectors are joined together.

The collar 2 of the Luer male connector 3 features an internal threading 5 whereas the Luer female connector 4 contains the largest of the rims 6 that fit to the internal threading 5 of the collar 2 of the Luer male connector so that the two parts can join.

Connecting the two Luer connections 1, 4 is accomplished simply by means of a tightening torque. The application of this tightening torque, or twisting movement, gives rise to a rotating movement of the Luer female connection 4 around the internal threading 5 of the male connector collar 2.

When the two Luer connectors 1, 4 are thus engaged and directly attached to each other, abrupt separation and contamination from without of these Luer connectors are prevented as described in ISO standard 594-2 of the International Organization of Standardization.

This standard also prescribes specific dimensions for each of the Luer connections.

While these Luer connectors 1, 4 are easy to use, handling errors by users have been observed during the coupling action in a large number of Luer connectors.

In particular, where handling is required in aphaeresis, there is a risk of inverting the two lines, for example anticoagulants and saline solution, when the lines both have identical Luer connectors.

As such, there is an urgent need to come up with other connectors that are different from state of the art connectors so as to avoid handling errors that could result in a risk to the health of patients.

Moreover, fluids transfer systems recognized as state of the art that prevent improper connections are generally complex structures comprised of a large number of initially distinct parts. It takes a lot of time to assemble these fluid transfer systems and they are costly.

The objective of this invention is to overcome this drawback by providing a fluids transfer system for medical use that is particularly simple in terms of design and operational use, that is aseptic and low cost and that affords a fully secure connection of Luer male and female connectors.

BRIEF DESCRIPTION OF THE INVENTION

The invention involves a fluids transfer system for medical use comprising a Luer male connector and a Luer female connector, of which the said Luer female connector comprises a main body containing an internal channel for the passage of said fluids and a collar surrounding at least a part of the end of the main body, while the said Luer male connector comprises a main body with a longitudinal internal opening.

According to the invention,

The main body of the female connector contains a first threading on at least a part of the external surface of that portion that is surrounded by the collar, located at least in part facing an internal surface of the collar, One of the ends of the main body of the said Luer male connector contains a second threading on at least a part of its internal surface delineating the longitudinal internal opening, which engages into and fits in the initial threading to ensure joining between the Luer male and female connectors, At least the external surface of the Luer male connector end where the second threading is located forms a conical male portion having a conical axis of revolution, while the said interior surface of the collar of the said female connector forms a conical female connecting surface having a conical axis of revolution, so that the external surface of the said male conical part fits against the conical connecting surface of the collar of the Luer female connector to provide a sealed joint when the Luer male and female connectors are fitted together.

Luer male and female connectors are disengaged by means of a disconnecting torque motion.

The locking system made up by the first and second helix threads of the Luer male and female connectors is located between the fluids passage area and the sealing space of the fluids transfer system, formed by the contact between the conical male portion and the conical female connecting surface. This locking system works to dispel constraints by reducing pressure exerted on the sealing space during fluids transfer in such a way as to preserve the space, thus preventing any occurrence of contamination or leakage.

In order to reinforce the sealed fit of the Luer male and female connectors, the collar of the Luer female connector may be elongated so as to present a larger conical female connection surface, while the external surface of the conical male portion is also increased through an elongation of the male conical piece.

In the various particular embodiments of this system, each with its particular advantages and possibilities for implementing numerous technical combinations:

At least one of the Luer male and female connectors is made as a single piece of plastic material, The Luer male connector features a collar, or skirt, that surrounds the male conical portion having a conical axis of revolution, at least partially so as to protect this conical male portion.

This advantageously protects against the risk of scratches forming on the conical male portion and against external contamination during storage of the Luer connector. Naturally, the internal diameter of the collar is such that the collar of the Luer female connector fits within this collar surrounding the conical male portion when the Luer male and female connectors are joined.

The diameter of the internal longitudinal opening of the said Luer male connector at the base of the said second threading is equal, within 0.2 mm, to the diameter of the main body of the Luer female connector with respect to its exterior threading, Some play will apply advantageously in the initial joining assembling part of the Luer male and female connector so that engaging the screw is facilitated for users, but this play will be reduced at the end of the screw phase to prevent any transfer of fluid.

Consequently, there may be a forced connection acting on these two connectors on a part of the threaded connection corresponding to the end joining phase of the Luer male and female connectors.

said Luer male connector, and/or the Luer female connector, contains an internal wall located in its internal longitudinal opening, respectively and/or in its internal channel, with the said internal wall comprising an orifice for the flow of fluids.

It is preferable, concerning the Luer male connector with an internal wall onto which an orifice is located at its internal longitudinal opening, that the orifice contain a truncated part located on the side of the end of the internal longitudinal opening that contains a second threading, so as to ensure that fluids are directed into the internal channel at the end of the main body of the female Luer connector when this end is placed close to the orifice in the internal wall.

The Luer female connector collar rotates or does or does not rotate around the female conical connector At least one of the Luer male and female connectors has a sealed end that ensures a link to the main body that is either whole or can be split.

This end is, from a purely illustrative perspective, a split blocking element to guarantee its asepsis.

The invention also concerns a Luer male connector intended for use in the fluids transfer system for medical use as described previously.

According to the invention, this connector comprises

A main body containing a longitudinal internal opening,

One of the ends of the main body of the Luer connector contains a thread on at least a part of its internal surface delineating the longitudinal internal opening, which engages into and fits in the threading of a Luer female connector to ensure a secure fit between the Luer male and female connectors, At least the external surface of the Luer male connector end where the said threading is located forms a conical male portion having a conical axis of revolution, said conical male portion fitting against the conical female connecting surface onto the collar of the Luer female connector when the said Luer male and female connectors are fitted together.

The end of the male connector opposite that forming a conical male portion having a conical axis of revolution may contain gripping elements on its external surface to facilitate handling.

The invention also concerns a Luer female connector intended for use in the fluids transfer system for medical use as described previously.

According to the invention, this Luer female connector comprises:

A main body containing an internal channel for the passage of fluids and a collar surrounding at least a part of the end of the said main body, The main body of the female connector contains a first threading on at least a part of the external surface of that portion that is surrounded by the collar, located at least in part facing an internal surface of the collar, the internal surface of the collar of the said female connector forms a conical female connecting surface having a conical axis of revolution so that the external surface of the conical male part of a Luer male connector fits against said conical female connecting surface when the Luer male and female connectors are fitted together, said conical male part having a conical axis of revolution.

The main body of the Luer female connector surrounded by the collar includes at least a single orifice opening laterally that can advantageously allow communication of fluids between the internal channel and the area comprising the internal surface of the collar and the external surface of the piece in order to limit any loss of fluids during their transfer.

The invention also pertains to a medical device comprising at least one recipient containing a medical use fluid equipped with a fluid transfer system for medical uses as described previously.

This recipient may be, for purely illustration purposes, a flexible pouch or a bottle.

The invention also concerns a medical device consisting of a syringe with a Luer male connector or Luer female connector attached as described previously.

BRIEF DESCRIPTION OF DRAWINGS

Other particular benefits, objectives and features of this invention will appear from the following description, which is done with regard to the appended drawings for the purposes of description and which are in no way limiting, in which:

FIG. 12a) represents a Luer male connector shown in FIG. 6 and a state of the art female connector FIG. 12b) represents a Luer male connector shown in FIG. 6 and a state of the art male connector FIG. 12c) represents a Luer female connector shown in FIG. 5 and a state of the art male connector FIG. 12d) represents a Luer female connector shown in FIG. 5 and a state of the art female connector FIG. 12e) represents a Luer male connector shown in FIG. 6 and a state of the art Slip fit Luer connector FIG. 12f) represents a Luer female connector shown in FIG. 5 and a state of the art Slip fit Luer connector

DETAILED DESCRIPTION OF THE EMBODIMENTS OF THE INVENTION

Figure 1:
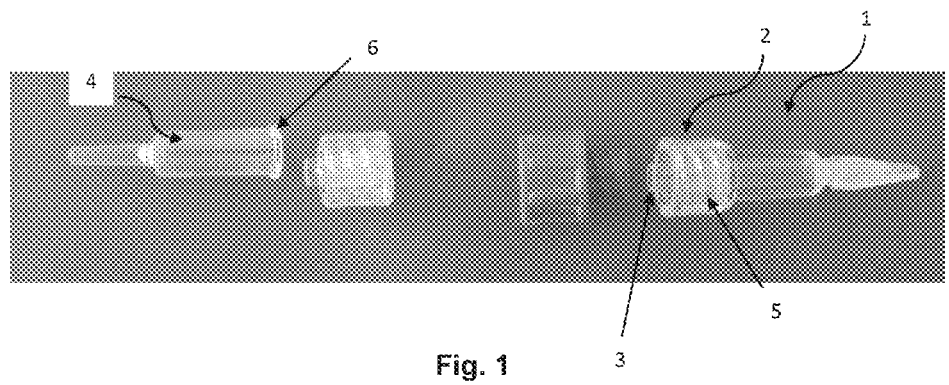
FIG. 1 is an overall view of the Luer male/female connector using prior art embodiment.
Figure 2:
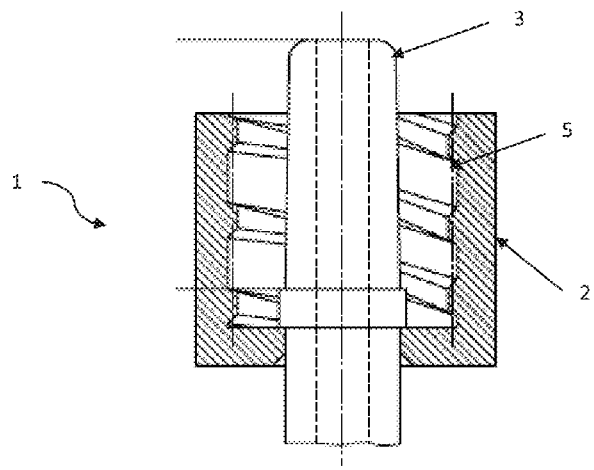
FIG. 2 is a partial section of the Luer male connector of FIG. 1.
Figure 3:
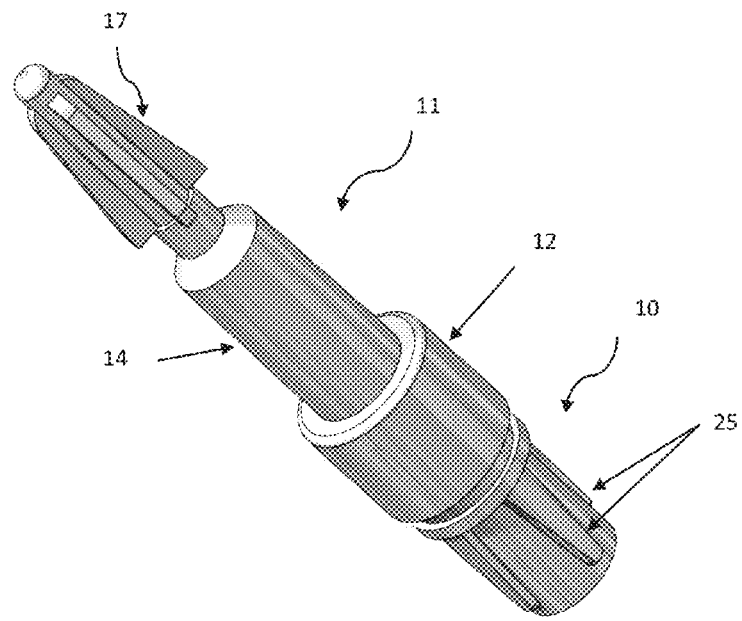
FIG. 3 is a side view of the fluids transfer system for medical use consisting of a Luer male connector and a Luer female connector, from an initial embodiment of the invention.
Figure 4:
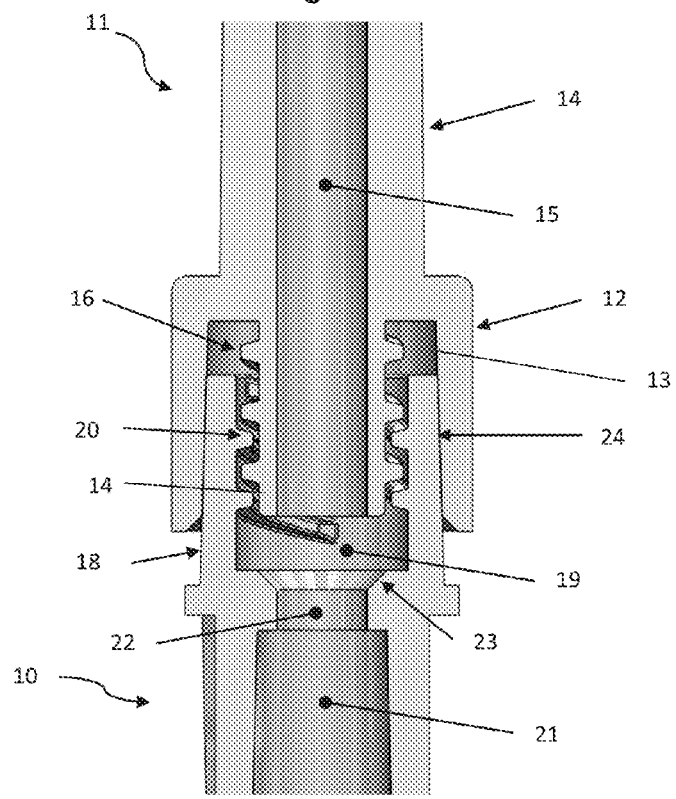
FIG. 4 is a partial view in longitudinal section of the fluids transfer system shown in FIG. 3.
Figure 5:
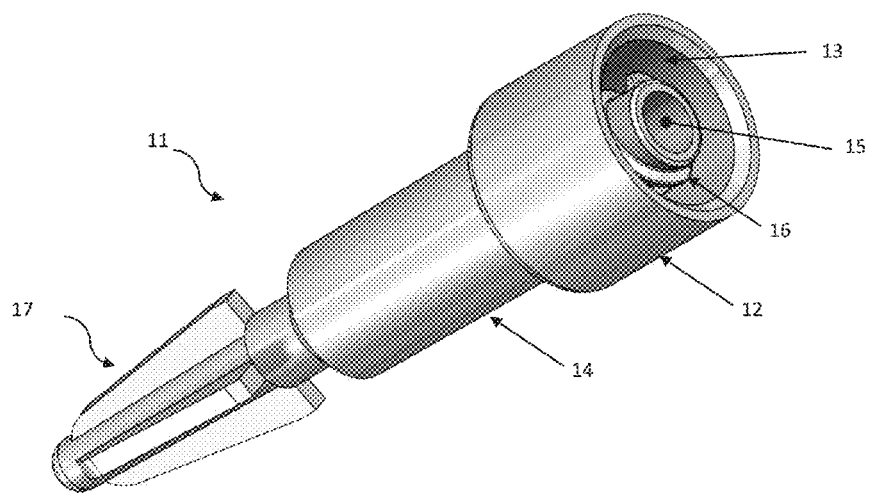
FIG. 5 is a side view of the Luer female connector of the fluids transfer system shown in FIG. 3.
Figure 6:
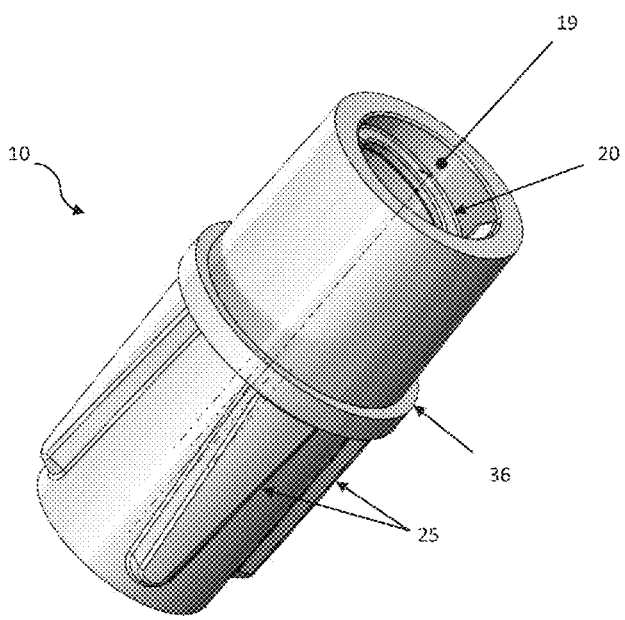
FIG. 6 is a side view of the Luer male connector of the fluids transfer system shown in FIG. 3.

It should first be noted that the drawings are not to scale.

FIGS. 3 to 6 are schematic representations of a fluids transfer system for medical use indicating the preferred embodiment of the invention.

This transfer system consists of a Luer male connector 10 and a Luer female connector 11 to be joined by means of tightening torque to enable the transfer of fluids.

The Luer female connector 11 features a fixed collar, or a skirt 12 with an internal surface 13 and an external surface. While the external surface of this collar 12 is cylindrical, its internal surface 13 presents a conical surface having a conical axis of revolution, said conical surface being smooth. This internal surface 13 thus forms a cone trunk with a taper angle of 6%, this surface being known as the female conical connection surface.

This collar 12 surrounds one end of a main body 14 of the Luer female connector 11. This main body 14 consists of an internal channel 15 for the passage of fluids.

This internal channel 15 has a diameter superior or equal to the diameter of the internal channel of the male conical portion of the Luer male connector set out in ISO standard 594-2. Thus the Luer female connector 11 presents a flow of medical solution at least equal to that of prior art Luer connectors. However, the diameter of the internal channel 15 is such that it is not possible to insert a male conical portion of a Luer male connector described in ISO standard 594-2.

This main body 14 also features an initial thread 16 on the external surface of its end surrounded by a collar 12, located opposite of the internal surface 13 of the collar 12.

Alternatively, the main body 14 end could be placed protruding from the collar 12, with a portion of the first thread 16 being located facing the internal surface 13 of the collar 12, while another portion of this threading would be located protruding from the collar.

This initial threading 16 is a constant pitch propeller as defined by ISO standard 594-2 and presents a trapezoidal profile that offers good resistance to wrenching.

The diameter of the main body 14 of the said Luer female connector 11 with respect to its exterior threading is beneficially too large to be able to be accidentally inserted into the internal channel of a Luer female connector described by ISO standard 594-2.

The main body 14 of the Luer female connector 11 features a conical profile on its end 17 opposite that surrounded by the collar 12, so that it can be inserted in a conduit such as tubing (not shown). This conical end 17 of the main body 14 of the Luer female connector 11 can alternatively be attached divisibly to the collar 12.

The end of the internal channel 15 located at the truncated end of the main body 14 of the Luer female connector 11 is advantageously blocked here by a removable stopping element.

The Luer male connector 10 includes a main body 18 containing an internal longitudinal opening. This internal longitudinal opening delineating an initial connecting area 19 that contains a second thread 20 which engages and fits into the initial threading to ensure a secure fit between the Luer male and female connectors, and a second connecting area 21 for receiving a tube.

This could be assembled at the wall of the main body 18 of the Luer male connector 10 delineating the second connection area 21 through joining by means of an adhesive solvent.

These two connection areas 19, 21 are separated by a wall bearing an orifice 22 that provides communication between these entities. This wall also constitutes a stopping point for the insertion of a tube in the second connection area 21.

The orifice 22 on this wall advantageously presents a flared portion 23 on the side of the connection area 19 so that with the Luer male and female connectors being joined, and an end of the internal channel of the main body 14 of the Luer female connector being located near this orifice 22, fluids leaving the internal channel 15 are directed toward the second connection area 21 of the Luer male connector 10 without contact with the second thread 20.

It should be noted that the internal diameter of the connection area 19 between the tops of two screw threads located facing each other is such that it cannot ensure that the conical male portion of a Luer male connector as described by ISO standard 594-2 will be maintained in place if inadvertently inserted in the connection area 19 when Luer male and female connectors are joined.

The end of the main body 18 of the Luer connector 10 that contains a connection area 19 presents an exterior surface 24 with a conical profile of a 6% taper.

This male conical portion 24 rests against the female conical connecting surface 13 of the collar 12 of the Luer female connector 11 when the Luer male and female connectors 10, 11 are joined so as to ensure a sealed fit. Moreover, the main body of the Luer male connector 10 contains gripping elements 25 on its external surface so as to facilitate handling, as well as a flange 36 located at the non-free end of the male conical portion 24. This flange 36 delineates the end of the male conical portion 24 and prevents contamination of this conical portion with the stopper.

These Luer male 10 and female 11 connectors are one piece units obtained through a mold by means of injecting a medically inert thermoplastic material. They may, for purely illustrative purposes, be of polycarbonate, polystyrene, acrylonitrile butadiene styrene (ABS) or PC-ABS copolymers, polyolefin (such as polyethylene, polypropylene, a homopolymer or a copolymer of polypropylene) or of a polyolefin comprising a thermoplastic elastomer (TPE) such as SEB (styrene, ethylene or butylene block copolymers), SEBS (styrene, ethylene, butylene, styrene block copolymers) or of cyclopolyolefin, etc.

The fluids transfer system of this invention is therefore particularly low cost to produce and does not require the assembly of several elements that would render the structure complex.

Advantageously, a user who must connect several pairs of connectors cannot erroneously connect a state of the art Luer female or male connector with a Luer male or female connector produced as a result of this invention.

Figure 7:
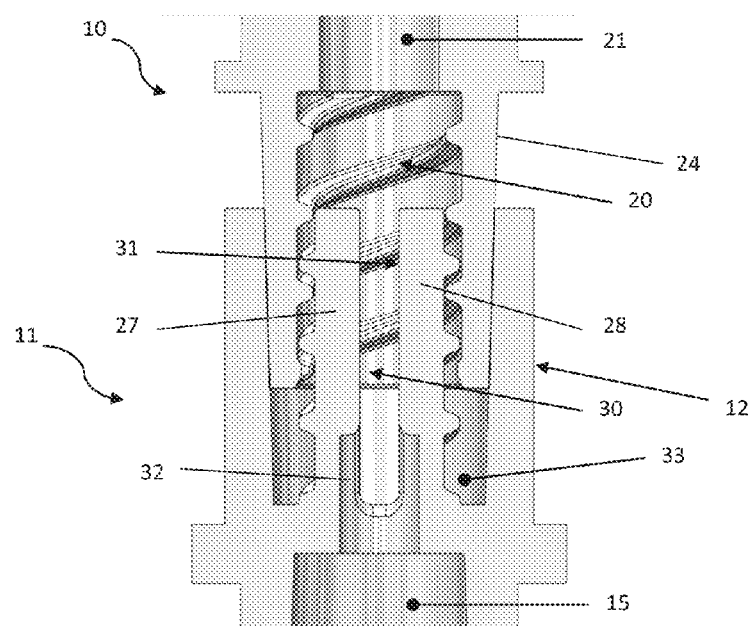
FIG. 7 is a partial sectional view of the fluids transfer system for medical use consisting of a Luer male connector and Luer female connector, from a second embodiment of the invention.
Figure 8:
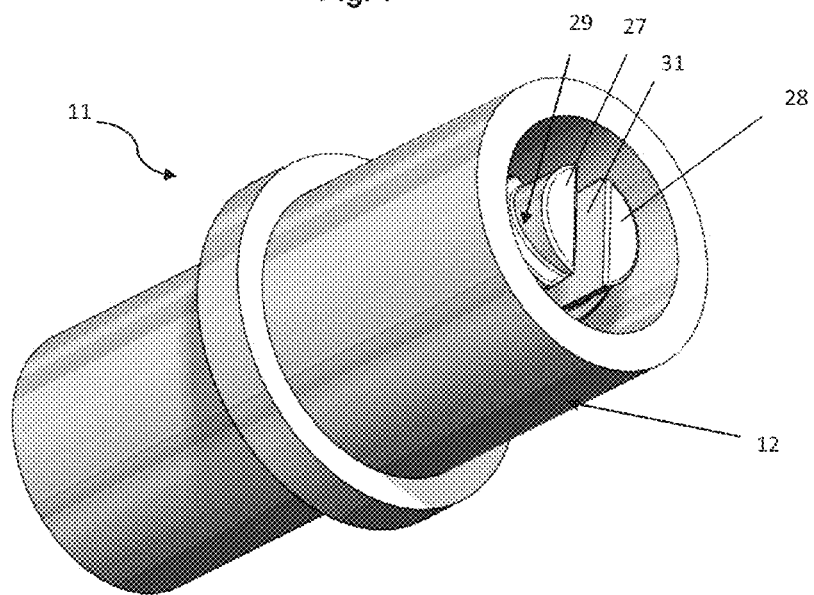
FIG. 8 is a side view of the Luer female connector of the fluids transfer system shown in FIG. 7.
Figure 9:
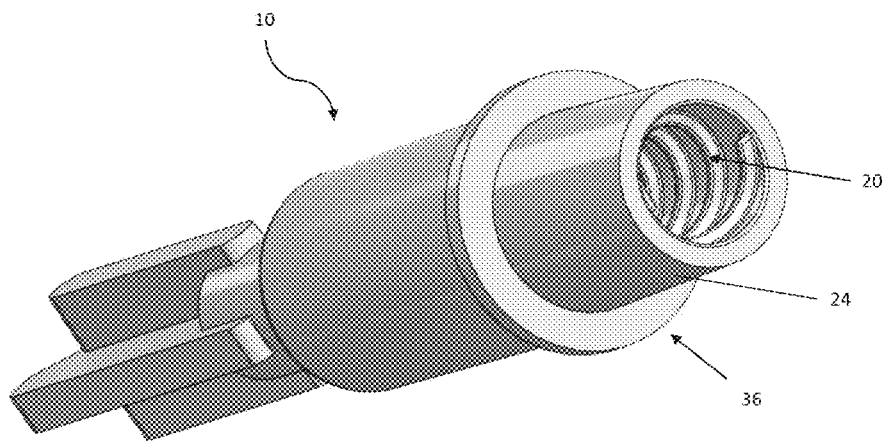
FIG. 9 is a side view of the Luer male connector of the fluids transfer system shown in FIG. 7.

FIGS. 7 to 9 are schematic representations of a fluids transfer system for medical use according to another embodiment of the invention. The elements of FIGS. 7 to 9 bear the same references as the elements of FIGS. 3 to 6 that represent the same objects, which will not be described again here.

The fluids transfer system in FIG. 7 differs from that described above in that the end of the main body of the Luer female connector 11 surrounded by the collar 12 is made up of two half cylindrical parts 27, 28 that are spaced apart from each other and parallel.

Each of the parts 27, 28 contain a portion of the helical thread 29 on its rounded exterior surface, with the threads on the exterior surface of one of the parts continuing on the exterior surface of the other half-cylindrical part such that a semi-continuous threading is formed that will match the threading 20 located on the internal surface of the main body 18 of the Luer male connector 10 to ensure that the Luer male and female connectors join up.

Moreover, following joining of the Luer male and female connectors, the internal cylindrical surface of the connecting area 19 of the Luer male connector, containing the second threading 20, surrounds the two half-cylindrical parts 27, 28 on at least a part of their longitudinal extension.

The component formed by the internal surface parts of the connection area 19 between the two half-cylindrical parts 27, 28 that are spaced apart from each other and the flat surfaces 30, 31 facing the two half-cylindrical parts make up a channel for the circulation of fluids. These fluids are then directed toward the second connection area 21 in the internal longitudinal opening of the Luer male connector 10.

The channel thus formed by the assembly of the Luer male and female connectors is in fluid communication with a chamber 32 formed at the base of the two half-cylindrical parts 27, 28, this chamber 32 being itself in fluid communication with both an internal channel 15 of the Luer female connector 11 for the passage of fluids with said channel 15 located at the other end of the Luer female connector 11, and with the base 33 of the collar 12 connected to the Luer female connector 11.

In this way any discharge that may occur along the threads between the internal cylindrical surfaces of the connection area of the Luer male connector and rounded exteriors of the two half-cylindrical parts will be recovered. Consequently, this ensures the minimizing of any loss of transferred fluid and the possible stagnation of fluids.

Figure 10:
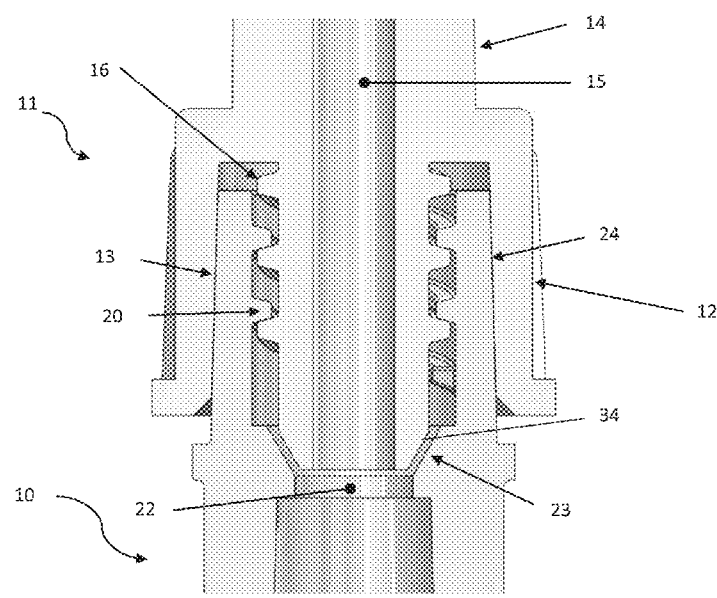
FIG. 10 is a partial side view of the fluids transfer system for medical use consisting of a Luer male connector and a Luer female connector, from a third embodiment of the invention.

FIG. 10 shows a partial view of the fluids transfer system for medical use in a third embodiment of the invention. The fluids transfer system in FIG. 10 differs from that described in FIGS. 3 to 6 in that the Luer male connector 10 with an internal wall containing an orifice 22 in its internal longitudinal opening has a truncated portion 23 located at the end of the internal longitudinal opening that has the said second threading 20, and the end of the main body of the Luer female connector 11 is conical 34 so that with this end being located near the orifice 22, 23 of the said internal wall, fluids are directed through the orifice. Advantageously, no fluid retention is observed with this fluids directional system.

These conical parts 23, 34 are kept away from contact with each other in order to avoid dual alignment.

Figure 11:
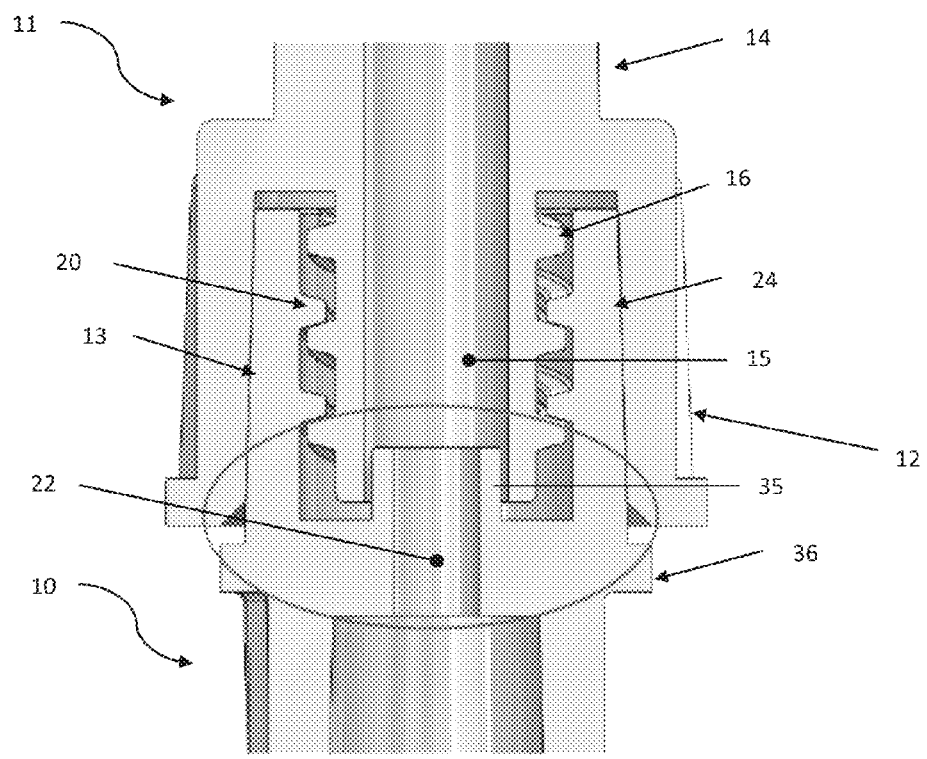
FIG. 11 is a partial side view of the fluids transfer system for medical use consisting of a Luer male connector and a Luer female connector, from a fourth embodiment of the invention.
Figure 12:
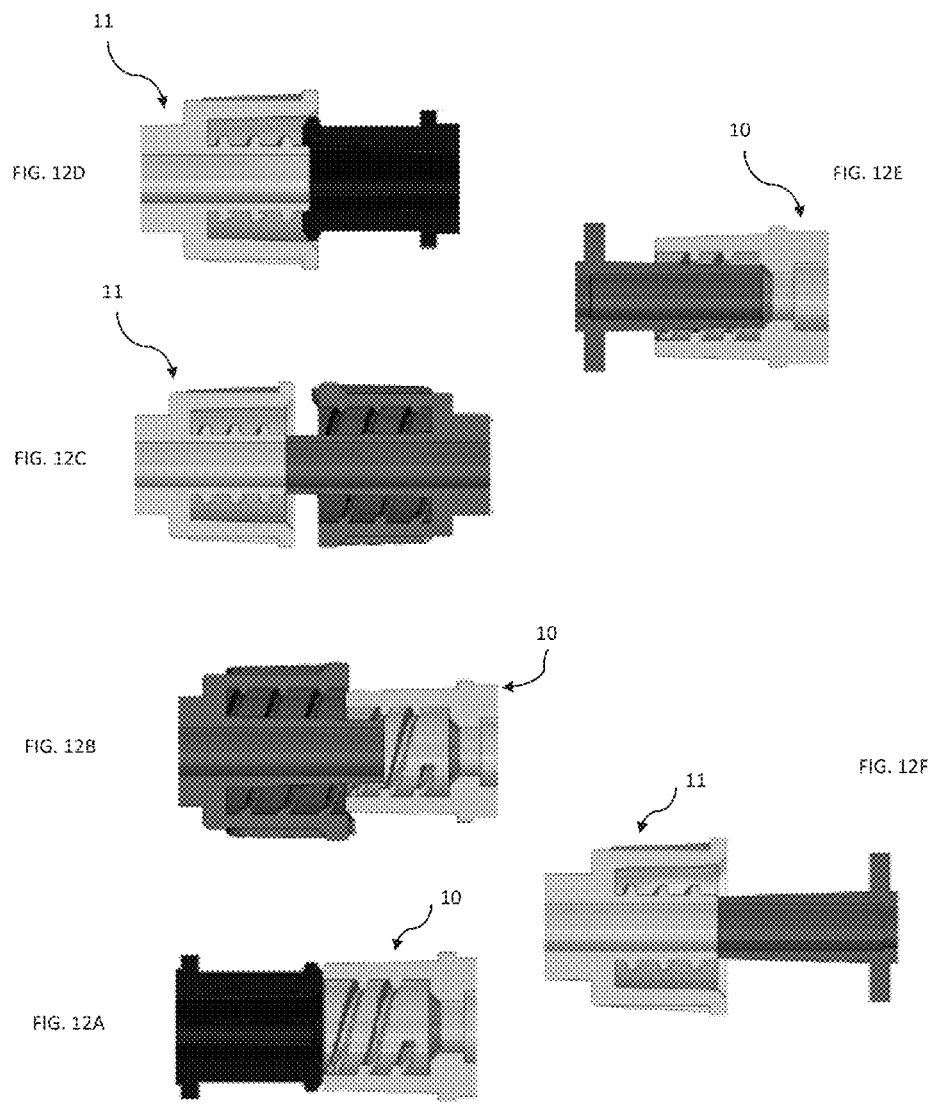
FIG. 12 represents partial sectional views showing unsuccessful attempts at joining a Luer male or female connector of FIGS. 3 to 6 and a prior art connector, specifically.

FIG. 11 shows a partial view of the fluids transfer system for medical use in a fourth embodiment of the invention. The fluids transfer system in FIG. 11 differs from that described in FIGS. 3 to 6 in that the Luer male connector 10 with an internal wall containing an orifice 22 in its internal longitudinal opening and this orifice has a portion 35 protruding from the said wall being located at the end of the internal longitudinal opening that has the before-mentioned second threading 20. This protruding portion 35, here for illustrative purposes a portion of a tube, has an external diameter inferior to the diameter of the internal channel 15 of the main body of the Luer female connector 11 so formed that it can be received in the internal channel 15 when the said Luer male 10 and female 11 connectors are joined so as to direct fluids through the said orifice 22.

This protruding part 35 and the wall of the main body of the Luer female connector delineating the internal channel 15 are kept away from contact with each other so as to avoid dual alignment.

The invention claimed is:

1. A fluids transfer system for medical use, comprising a Luer male connector (10) and a Luer female connector (11), wherein said Luer female connector (11) comprises a main body (14) containing an internal channel (15) for the passage of said fluids, and a collar (12) surrounding at least a part of the end of the main body, and said Luer male connector (10) comprises a main body (18) with a longitudinal internal opening (19, 21), and wherein:

the main body (14) of the female connector contains a first threading (16) on at least a part of the external surface of that portion that is surrounded by the collar (12), located at least in part facing an internal surface of the collar (12), one of the ends of the main body (18) of the Luer male connector (10) contains a second threading (20) on at least a part of its internal surface delineating the longitudinal internal opening (19, 21), which engages into and fits in the first threading (16) to ensure joining between the Luer male and female connectors, at least the external surface of the Luer male connector (10) end where the second threading (20) is located forms a conical male portion (24) having a conical axis of revolution, while the interior surface of the collar (12) of the female connector forms a conical female connecting surface (13) having a conical axis of revolution, so that the external surface of the male conical part (24) fits against the conical connecting surface of the collar (12) of the Luer female connector (11) to provide a sealed joint when the Luer male and female connectors are fitted together.

2. The system according to claim 1, characterized in that at least one of the Luer male (10) and female (11) connectors is made of a single piece and of plastic material.

3. The system according to claim 1, characterized in that the internal channel (15) of the Luer female connector (11) has a diameter at least equal to the diameter of the internal channel (15) of the male conical portion (24) of the Luer male connector (10) set out in ISO standard 594-2.

4. The system according to claim 1, characterized in that the Luer male connector (10), and/or the Luer female connector (11), contains an internal wall located in its internal longitudinal opening (19, 21), respectively and/or in its internal channel (15), with the internal wall comprising an orifice for the flow of fluids.

5. The system according to claim 4, characterized in that the Luer male connector (10) with an internal wall containing an orifice in its internal longitudinal opening (19, 21), which orifice has a truncated portion located at the end of the longitudinal internal opening (19, 21) that has a second threading (20), and the end of the main body of the Luer female connector (11) is conical so that with this end being located near the orifice of the said internal wall, fluids are directed through the orifice.

6. The system according to claim 4, characterized in that the Luer male connector (10) with an internal wall containing an orifice in its longitudinal internal opening (19, 21), which orifice has a portion protruding from the wall being located at the end of the longitudinal internal opening (19, 21) that comprises said second threading (20), with said protruding portion having an external diameter inferior to the diameter of the internal channel (15) of the main body of the Luer female connector (11) so that it can be received in the internal channel (15) when the Luer male and female connectors are joined together in order to direct said fluids through the orifice.

7. The system according to claim 4, characterized in that the internal channel (15) of the Luer female connector (11) has a diameter at least equal to the diameter of the internal channel (15) of the male conical portion (24) of the Luer male connector (10) set out in ISO standard 594-2.

8. A medical device that includes at least one recipient containing fluids for medical use equipped with the fluids transfer system according to claim 1.

9. The system according to claim 2, characterized in that the internal channel (15) of the Luer female connector (11) has a diameter at least equal to the diameter of the internal channel (15) of the male conical portion (24) of the Luer male connector (10) set out in ISO standard 594-2.

10. The system according to claim 2, characterized in that the Luer male connector (10), and/or the Luer female connector (11), contains an internal wall located in its internal longitudinal opening (19, 21), respectively and/or in its internal channel (15), with the internal wall comprising an orifice for the flow of fluids.

11. A medical device that includes at least one recipient containing fluids for medical use equipped with the fluids transfer system according to claim 2.

* * * * *